(12) United States Patent
Zhou et al.

(10) Patent No.: US 6,541,639 B2
(45) Date of Patent: Apr. 1, 2003

(54) EFFICIENT LIGAND-MEDIATED ULLMANN COUPLING OF ANILINES AND AZOLES

(75) Inventors: Jiacheng Zhou, Hockessin, DE (US); Pasquale N. Confalone, Greenville, DE (US); Hui-Yin Li, Hockessin, DE (US); Philip Ma, West Chester, PA (US); Lynette M. Oh, West Chester, PA (US); Lucius T. Rossano, Landenberg, PA (US); Charles G. Clark, Cherry Hill, NJ (US); Chris Teleha, Bear, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/912,950

(22) Filed: Jul. 25, 2001

(65) Prior Publication Data

US 2002/0099225 A1 Jul. 25, 2002

Related U.S. Application Data

(60) Provisional application No. 60/220,932, filed on Jul. 26, 2000.

(51) Int. Cl.[7] ...................... C07D 211/02; C07D 249/04
(52) U.S. Cl. .................. 546/249; 546/250; 546/274.1; 548/255; 548/265.8; 548/343.5; 548/563
(58) Field of Search ............................ 548/343.5, 563, 548/255, 265.8; 546/249, 250, 274.1

(56) References Cited

U.S. PATENT DOCUMENTS 5,705,697 A    1/1998   Goodbrand

FOREIGN PATENT DOCUMENTS

| JP | 63072658 A | 2/1988 |
|---|---|---|
| WO | WO 9857951 A | 12/1998 |

OTHER PUBLICATIONS

Venuti, M. C. et al. "Inhibitors of Cyclic AMP Phosphodiesterase. 3. Synthesis and Biological Evaluation of Pyrido and Imidazolyl Analogues of 1,2,3,5–Tetrahydro–2–oxoimidazo[2,1,β]quinazoline" J. Med. Chem., 1988, 31(11), pp. 2136–2145.

Kiyomora, A. et al. "An Efficient Copper–Catalyzed Coupling of Aryl Halides with Imidazoles" Tetrahedron Letters, 1999, 40(14), pp. 2657–2660.

Khan, M. A. et al. "Synthesis of Heterocyclic Compounds. Part II. N–Arylazoles by Ullmann Condensation" J. Chem. Soc., 1970, 1, pp. 85–91.

Bacon, R. G. R. et al. "Metal Ions and Complexes in Organic Reactions. Part IX. Copper(I)–catalysed Conversion of Aryl Halides into Alkyl Aryl Ethers" J. Chem. Soc. (C), 1969, pp. 312–315.

Ragan, J. A. et al. "2,5–Dimethylpyrrole Protection Facilitates Copper(I)–Mediated Methoxylations of Aryl Iodides in the Presence of Anilines" Synthesis, 1998, 11, pp. 1599–1603.

*Primary Examiner*—Joseph K. McKane
*Assistant Examiner*—Andrea D. Small
(74) *Attorney, Agent, or Firm*—David H. Vance

(57) ABSTRACT

The present invention provides of method of preparing phenyl-substituted azoles. This method uses an efficient ligand-accelerated Ullmann coupling reaction of anilines with azoles. The coupling products are useful for preparing factor Xa inhibitors.

29 Claims, No Drawings

EFFICIENT LIGAND-MEDIATED ULLMANN COUPLING OF ANILINES AND AZOLES

This application claims benefit of No. 60/220,932 Jul. 26, 2000.

FIELD OF THE INVENTION

This invention relates generally to an efficient ligand-accelerated Ullmann coupling reaction of anilines with azoles. The coupling products are useful for preparing factor Xa inhibitors.

BACKGROUND OF THE INVENTION

Factor Xa inhibitors like those of Formulas Ia and Ib shown below:

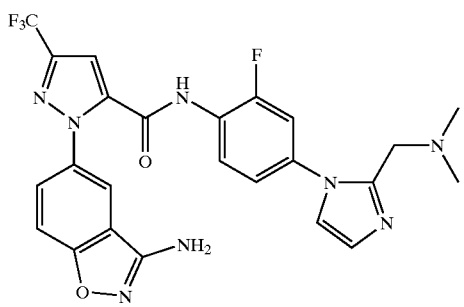

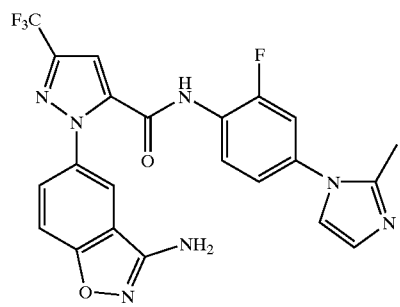

are currently being investigated as potential drug candidates. As a result, large quantities of these compounds are needed to satisfy clinical demands.

WO98/57951 describes of the synthesis of compounds of formula Ia and Ib as shown below.

Procedure Ia

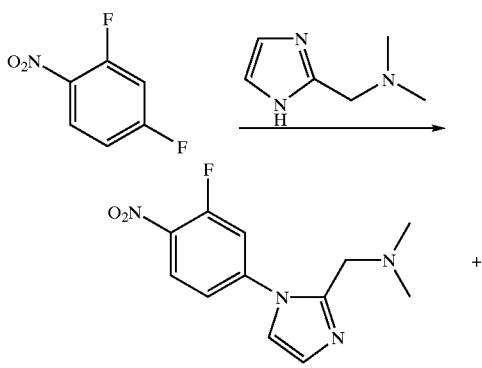

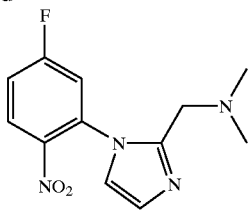

Procedure Ib

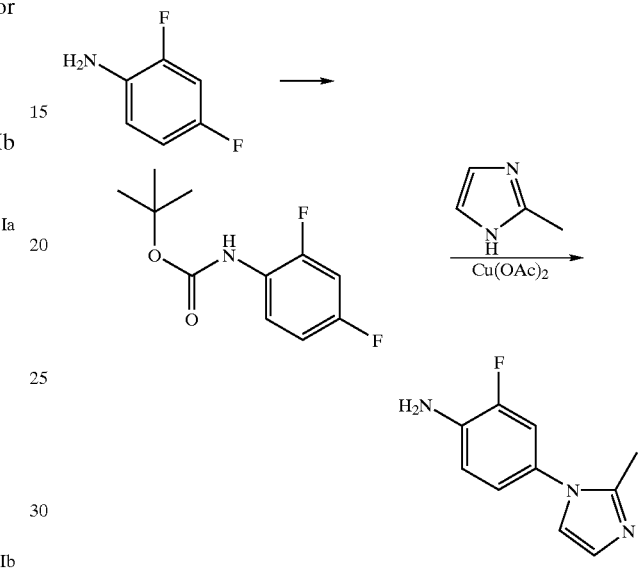

In procedure Ia, the resulting imidazolyl-aniline is coupled with 1-(3-cyano-4-fluorophenyl)-3-trifluoromethyl-5-pyrazole carboxylic acid and the resulting intermediate is then converted to the final product. Procedure Ia is problematic in that it provides isomers of the imidazolyl-nitrobenzene. In procedure Ib, the resulting imidazolyl-aniline is coupled with 1-(3'-aminobenzisoxozol-5-yl)-3-trifluoromethyl-5-pyrazolecarboxylic acid to provide the final product. Procedure Ib is problematic in that it only provides a 48.5% yield of the imidazolyl-aniline intermediate starting from the bromo-fluoroaniline.

Many different kinds of aryl halides have been used as substrates for the Ullmann-type amination reaction. This most straightforward route to N-(amino)arylimodazoles involves the direct formation of the aromatic carbon-nitrogen bond under the catalysis of a copper(I) salt without protection of the aromatic amino functionality. However, there is almost no precedent to directly employ unprotected aniline derivatives as coupling partners. The free NH$_2$ functionality on the aryl halides is reported to have a deleterious effect (35–50% yields of unprotected aniline substrates vs 75–100% yields of non-aniline substrates or protected aniline substrates) on the Ullmann coupling reaction (*J. Chem. Soc.* (C) 1969, 312). One report revealed that direct coupling of 4-iodoaniline with imidazole under the Cu(I)-catalyzed condition afforded the desired N-(4-amino) arylimidazole only in 37% yield (*J. Med. Chem.* 1988, 31, 2136). Another report observed that no coupling products was obtained when unprotected 2-fluoro-4-iodoaniline was exposed to the Ullmann ether synthesis (*Synthesis,* 1998, 1599). In that report, the authors also found that protection of the aromatic amino group to amide or carbamate before being subjected to the Ullmann coupling reaction resulted only in the cleavage of the protection group without formation of any desired coupling product. Therefore, a hydrolytically stable 2,5-dimethylpyrrole derivative of that aniline substrate was prepared. Obviously, two more steps (protection and deprotection) is added to the synthetic sequence in order to form the aromatic carbon-nitrogen or carbon-oxygen bond when the halogenated aniline is used as the coupling substrate.

It can be seen that preparation of factor Xa inhibitors, specifically preparation of azolyl-aniline intermediates useful therein, is difficult. Thus, it is desirable to find efficient syntheses azolyl-anilines that are useful in making factor Xa inhibitors of compounds like those of formulas Ia and Ib.

SUMMARY OF THE INVENTION

Accordingly, one object of the present invention is to provide novel processes for preparing azolyl-anilines using a ligand-mediated Ullmann coupling reaction.

These and other objects, which will become apparent during the following detailed description, have been achieved by the inventors' discovery that imidazolyl-anilines like those shown below (formulas IIa and IIb):

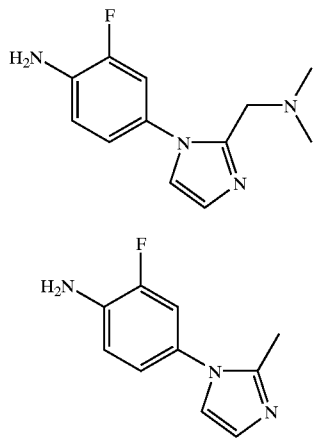

can be prepared by ligand-accelerated Ullmann coupling of non-protected, halo-substituted anilines and azoles. This is the first time an Ullmann coupling of an aniline has been shown to work efficiently without protection of the aniline nitrogen.

DETAILED DESCRIPTION OF PREFERRED EMBODIMENTS

The present invention demonstrates that Cu(I)-catalyzed coupling of iodoanilines to imidazoles is accelerated by a group of hydrolytically stable ligands known to coordinate Cu(I) catalyst. The ligands, preferably the alkyl and aryl bidentate nitrogen and oxygen containing compounds, used in an equimolar amount with respect to Cu(I) catalyst, are found to produce the significant rate acceleration for the coupling reaction. The reaction temperature (100–130° C. vs >150° C.) is significantly lower and the reaction time (4–6 h vs 16–24 h) is significantly shorter with this ligand-accelerated protocol. And also, the coupling yield is improved with the addition of the ligand.

The present method is the first reported actual ligand-accelerated Cu(I)-catalyzed Ullmann coupling of the aryl halides to azoles, including imidazoles. Both Cu(I) salt and ligand used in this method are used in catalytical amounts (5–15%). In the previous reports, both Cu(I) catalyst and ligand were employed excessively (0.2 to 2.0 equivalents).

In contrast to Buchwald's report (*Tetrahedron Lett.* 1999, 40, 2657), which is the only reported ligands-accelerated Ullmann coupling of aryl halides to imidazoles so far, this method uses only one additive to be as the ligand to promote the reaction. Instead of the use of 10-fold excess of the ligand with respect to the Cu(I) catalyst (*Tetrahedron Lett.* 1999, 40, 2657), the method detailed of the present invention employs the equimolar amount of ligand with respect to the copper catalyst.

In an embodiment, the present invention provides a novel process for making a compound of Formula III:

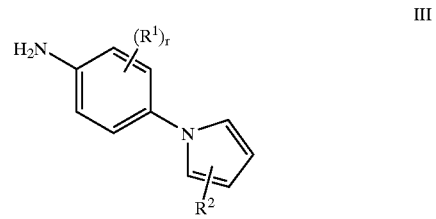

comprising: contacting an aniline of Formula IV with an azole of Formula V in the presence of $Cu(I)X^1$ and a bidentate ligand:

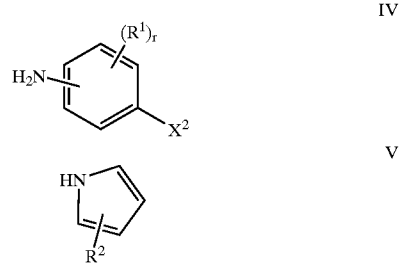

wherein:
in Formula IV, from 0–1 of the carbon atoms are replaced with N;
in Formula V, from 0–3 of the carbon atoms are replaced with N;
alternatively, the compound of Formula V is benzo-fused and 0–2 of the carbon atoms of the five-membered ring are replaced with N;
$X^1$ is selected from Cl, Br, I, and SCN;
$X^2$ is selected from Br or I;
$R^1$ is selected from H, Cl, F, Br, I, $C_{1-4}$ alkyl, $C_{1-4}$ alkoxy, $C_{1-4}$ alkylene-O—$C_{1-4}$ alkyl, $NH_2$, $NH(C_{1-4}$ alkyl), $N(C_{1-4}$ alkyl$)_2$, $C_{1-4}$ alkylene-$NH_2$, $C_{1-4}$ alkylene-NH ($C_{1-4}$ alkyl), $C_{1-4}$ alkylene-N($C_{1-4}$ alkyl$)_2$, $C_{3-10}$ carbocycle substituted with 0–2 $R^3$, 5–6 membered heterocycle comprising carbon atoms and 1–4 heteroatoms selected from N, O, and S and substituted with 0–2 $R^3$;
$R^2$ is selected from H, Cl, F, Br, I, $C_{1-4}$ alkyl, $C_{1-4}$ alkoxy, $C_{1-4}$ alkylene-O—$C_{1-4}$ alkyl, $NH_2$, $NH(C_{1-4}$ alkyl), $N(C_{1-4}$ alkyl$)_2$, $C_{1-4}$ alkylene-$NH_2$, $C_{1-4}$ alkylene-NH ($C_{1-4}$ alkyl), $C_{1-4}$ alkylene-N($C_{1-4}$ alkyl$)_2$, $C_{3-10}$ carbocycle substituted with 0–2 $R^3$, 5–6 membered heterocycle comprising carbon atoms and 1–4 heteroatoms selected from N, O, and S and substituted with 0–2 $R^3$;
$R^3$ is selected from Cl, F, Br, I, $C_{1-4}$ alkyl, $C_{1-4}$ alkoxy, $C_{1-4}$ alkylene-O—$C_{1-4}$ alkyl, $NH_2$, $NH(C_{1-4}$ alkyl), $N(C_{1-4}$ alkyl$)_2$, $C_{1-4}$ alkylene-$NH_2$, $C_{1-4}$ alkylene-NH ($C_{1-4}$ alkyl), $C_{1-4}$ alkylene-N($C_{1-4}$ alkyl$)_2$, and $NO_2$;

r is 1 or 2; and, the bidentate ligand is a hydrolytically stabile ligand that is known to ligate with Cu(I) and comprises two heteroatoms selected from N and O.

In a preferred embodiment, the bidentate ligand is selected from tetramethylethylenediamine (TMED), 2,2'-dipyridyl (DPD), 8-hydroxyquinoline (HQL), and 1,10-phenanthroline (PNT) and from 0.01–0.20 equivalents are present, based on the molar amount of aniline present.

In another preferred embodiment, the bidentate ligand is 8-hydroxyquinoline (HQL) or 1,10-phenanthroline (PNT) and from 0.05–0.15 equivalents are present.

In another preferred embodiment, the bidentate ligand is 8-hydroxyquinoline (HQL) and from 0.05–0.15 equivalents are present.

In another preferred embodiment, the bidentate ligand is 1,10-phenanthroline (PNT) and from 0.05–0.15 equivalents are present.

In another preferred embodiment, from 0.01–0.20 equivalents of Cu(I)$X^1$ are present, based on the molar amount of aniline present.

In another preferred embodiment, from 0.05–0.15 equivalents of Cu(I)$X^1$ are present.

In another preferred embodiment, 0.05 equivalents of Cu(I)$X^1$ are present.

In another preferred embodiment, 0.15 equivalents of Cu(I)$X^1$ are present.

In another preferred embodiment, the contacting is performed in the presence of from 1.0–2.0 molar equivalents of base, based on the molar amount of aniline present.

In another preferred embodiment, the contacting is performed in the presence of from 1.0–1.2 equivalents of $K_2CO_3$.

In another preferred embodiment, the contacting is performed in the presence of 1.05 equivalents of $K_2CO_3$.

In another preferred embodiment, from 1–1.5 molar equivalents of azole are used, based on the molar amount of aniline present.

In another preferred embodiment, from 1.1–1.3, molar equivalents of azole are used, based on the molar amount of aniline present.

In another preferred embodiment, from 1.2 molar equivalents of azole are used, based on the molar amount of aniline present.

In another preferred embodiment, the contacting is performed in a polar solvent.

In another preferred embodiment, the contacting is performed in a polar, aprotic solvent.

In another preferred embodiment, the contacting is performed in DMSO.

In another preferred embodiment, the contacting is performed at a temperature of from 100° C. to reflux of the solvent and the reaction is run from 4 to 24 hours.

In another preferred embodiment, the contacting is performed at a temperature of from 110 to 140° C. and from 6 to 15 hours.

In another preferred embodiment, the contacting is performed at a temperature of from 120 to 130° C.

In another preferred embodiment, $X^1$ is I or SCN.

In another preferred embodiment, $X^1$ is I.

In another preferred embodiment, $X^1$ is SCN.

In another preferred embodiment, Formula V is an imidazole;
  alternatively, the compound of Formula V is a benzo-fused imidazole;
  $R^1$ is selected from H, Cl, F, methyl, ethyl, i-propyl, methoxy and, methoxymethylene;

$R^2$ is selected from H, methyl, i-propyl, $NH_2$, $CH_2NH_2$, $CH_2N(CH_3)_2$, and phenyl; and, r is1.

In another preferred embodiment, the compound of Formula IV is selected from:

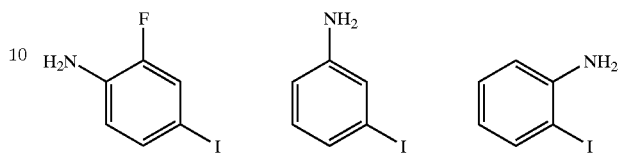

IV and, the compound of Formula V is selected from:

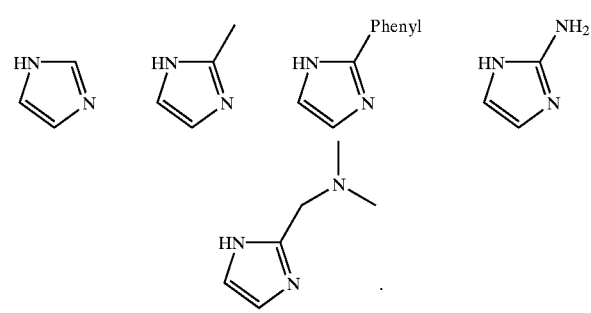

V

In another preferred embodiment, the compound of Formula IV is:

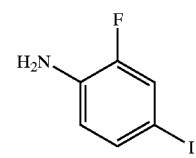

IV and, the compound of Formula V is selected from:

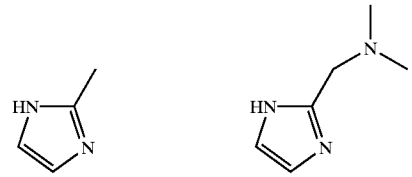

V

In another preferred embodiment, the compound of Formula V is:

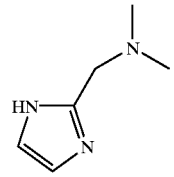

V

In another preferred embodiment, the compound of Formula V is:

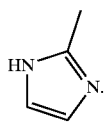

Definitions

As used herein, the following terms and expressions have the indicated meanings. It will be appreciated that the compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

The processes of the present invention are contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^1$) occurs more than one time in any constituent or formula for a compound, its definition at each occurrence is independent of its definition at every other occurrence. Thus, for example, if a group is shown to be substituted with 0–2 $R^1$, then said group may optionally be substituted with up to two $R^1$ groups and $R^1$ at each occurrence is selected independently from the definition of $R^1$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon-carbon bonds that may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon-carbon bonds that may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

As used herein, "carbocycle" or "carbocyclic group" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The reactions of the synthetic methods claimed herein are preferably carried out in the presence of a suitable base, said suitable base being any of a variety of bases, the presence of which in the reaction facilitates the synthesis of the desired product. Suitable bases may be selected by one of skill in the art of organic synthesis. Suitable bases include, but are not limited to, inorganic bases such as alkali metal, alkali earth metal, thallium, and ammonium hydroxides, alkoxides, phosphates, and carbonates, such as sodium hydroxide, potassium hydroxide, sodium carbonate, potassium carbonate, cesium carbonate, thallium hydroxide, thallium carbonate, tetra-n-butylammonium carbonate, and ammonium hydroxide.

The reactions of the synthetic methods claimed herein are carried out in suitable solvents which may be readily selected by one of skill in the art of organic synthesis, the suitable solvents generally being any solvent which is substantially non-reactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

Preferably, the contacting is performed in a suitable polar solvent. Suitable polar solvents include, but are not limited to, ether and aprotic solvents.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, or t-butyl methyl ether.

Suitable aprotic solvents may include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Synthesis

The processes of the present invention can be practiced in a number of ways depending on the solvent, base, chiral moderator, and temperature chosen. As one of ordinary skill in the art of organic synthesis recognizes, the time for reaction to run to completion as well as yield and enantiomeric excess will be dependent upon all of the variables selected.

Aniline Substrate

Under the same reaction conditions, the coupling reaction with iodoanilines as the substrates was found to be faster than that with the corresponding bromoanilines as the substrates. This reactivity difference between iodoanilines and bromoanilines is found to be even greater without ligand acceleration. Without the ligand acceleration, the coupling of bromoanilines to azoles takes 24 to 48 hours to completion while the coupling of iodoanilines to azoles is complete in 10–20 hours at the same reaction temperature (120–130° C.). However, the coupling reaction of either iodoanilines or bromoanilines to azoles is significantly accelerated when an equimolar amount of ligand, such as 8-hydroxyquinoline, is employed. This ligand-acceleration is especially remarkable for the bromoanilines. With the addition of the ligand, the coupling reaction of bromoanilines to imidazoles reaches completion in 6 to 8 hours at the same reaction temperature (120–130° C.). Therefore, with this ligand acceleration, both iodoanilines and bromoanilines are suitable coupling substrates, even though the former substrate provides the faster reaction rate. The preferred substrate is an iodoaniline.

Cu(I) Catalyst

The Cu(I) catalyst is preferably a Cu(I) salt selected from CuCl, CuBr, CuBr-SMe$_2$, CuSCN, CuI, and CuOTf. More preferably, the Cu(I) catalyst is selected from CuCl, CuSCN, and CuI. A more preferred Cu(I) catalyst is CuSCN. Another more preferred Cu(I) catalyst is CuI.

The amount of Cu(I) catalyst used depends on the selected starting materials and reaction conditions. Preferably, from 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, to 0.20 equivalents of Cu(I)X are present. More preferably, from 0.05, 0.06, 0.07, 0.08, 0.09, 0.10, 0.11, 0.12, 0.13, 0.14, to 0.15 equivalents of Cu(I)X are present. An even more preferred amount of catalyst is 0.05 equivalents. Another even more preferred amount of catalyst is 0.15 equivalents. For large scale reactions, it is preferred that about 0.05 equivalents of CuI is used.

Ligand

Rate accelerations have been reported in the industrially important Ullmann ether condensation reaction. Several different kinds of organic molecules, such as alkyl formates or simple alkyl carboxylates and alkyl and aryl monodentate and bidentate nitrogen/oxygen containing compounds, were found to be able to affect the catalyst (copper(I) salt) competency in the Ullmann condensation reactions. Those compounds are found to possess the ability to ligate the copper(I) catalyst. However, the Ullmann coupling reaction is normally conducted under the basic condition, the ligand used in this reaction, therefore, must be stable enough to coordinate the Cu(I) catalyst.

A bidentate ligand that is a hydrolytically stabile is useful in the present invention. The ligand should ligate with Cu(I) and comprises two heteroatoms selected from N and O. Preferably, the bidentate ligand is selected from tetramethylethylenediamine (TMED), 2,2'-dipyridyl (DPD), 8-hydroxyquinoline (HQL), and 1,10-phenanthroline (PNT). More preferably, the bidentate ligand is 8-hydroxyquinoline (HQL) or 1,10-phenanthroline (PNT). An even more preferred bidentate ligand is 8-hydroxyquinoline (HQL). An even more preferred bidentate ligand is 1,10-phenanthroline (PNT).

The amount of bidendate ligand present should be approximately equivalent to the amount of Cu(I) catalyst present. Thus, from 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, to 0.20 molar equivalents of bidentate ligand are present. More preferably, from 0.05, 0.06, 0.07, 0.08, 0.09, 0.10, 0.11, 0.12, 0.13, 0.14, to 0.15 equivalents of bidentate ligand are present. An even more preferred amount of bidentate ligand is 0.05 equivalents. Another even more preferred amount of bidentate ligand is 0.15 equivalents. For large scale reactions, it is preferred that about 0.05 equivalents of CuI is used.

Base

In this Ullmann coupling of iodoanilines to azoles, a base is preferred to scavenge the in situ generated hydrogen iodide (or hydrogen bromide). Moreover, this base can also serve to deprotonate the azole to form the corresponding azole anion, which is a more reactive coupling partner. Preferably this base is inorganic and more preferably weak. $K_2CO_3$ and $Cs_2CO_3$ are preferred bases. Potassium carbonate is preferred when a polar, aprotic solvent is used. Cesium carbonate is preferred if a less polar organic solvent is used.

The amount of base is preferably 1.0, 1.1, 1.2, 1.3, 1.4, 1.5, 1.6, 1.7, 1.8, 1.9, to 2.0 molar equivalents, more preferably 1.0 to 1.2 and even more preferably 1.05. In large scale reactions, it is preferable to use about 1.05 equivalents of $K_2CO_3$.

Mole Ratio of Aniline to Azole

The coupling reaction proceeds smoothly when the equal molar substrates are used. However, a significant amount of the unreacted iodoaniline is usually recovered. Therefore, it is preferable to use a slight excess amount of the azoles. The molar ratio of the aniline to azole is preferably 1, 1.1, 1.2, 1.3, 1.4, to 1.5. More preferably, the molar ratio is from 1.1, 1.2, to 1.3. Even more preferably, the molar ratio is about 1.2.

Solvent

Polar solvents can be used in the present invention. However, polar, aprotic solvents are preferred. DMSO is a preferred polar, aprotic solvent. Under the thermal condition, this polar, aprotic solvent promotes the deprotonation of the azole by the inorganic, weak base ($K_2CO_3$) to its corresponding anion, which is proven to be the better coupling partner. A ethylene glycol derivatives, such as ethylene glycol monoalkyl ethers, are also suitable solvents for this coupling reaction. Even though these solvents did not give the better results for this coupling reaction comparing to DMSO, their free hydroxyl group does not interfere the azole coupling with iodoanilines. With DMSO as solvent, the reaction concentration is preferably from 0.8 to 1.0 M. When DMSO is used on large scale, the preferred concentration is 1.0 M.

Oxygen, particularly the dissolved oxygen in the solvent, was found to interfere the coupling reaction significantly. First, it deactivates the catalyst by oxidation of copper salt. Secondly, it could oxidize the iodoanilines. Therefore, this Ullmann coupling reaction is preferably conducted strictly under a nitrogen atmosphere.

Temperature and Reaction Time

The Ullmann coupling of iodoanilines to azoles is a thermally promoted reaction. Thus, it is preferable to run the coupling reaction under heat. Preferably, the contacting is performed at a temperature of from 100° C. to reflux of the solvent and the reaction is run from 4 to 24 hours. More preferably, the contacting is performed at a temperature of from 110 to 140° C. and from 6 to 15 hours. Even more preferably, the contacting is performed at a temperature of from 120 to 130° C.

Workup

The work-up of the coupling reaction can be relatively difficult and time consuming. The desired coupling product is usually a hydrophilic material. Therefore, the amount of the aqueous solution used for quenching the reaction is preferably as small as possible and the organic solvent extraction process is repeated several times in order to get the good recovery of the product.

In a typical work-up process, a saturated $NH_4Cl$ aqueous solution or a 14% aqueous $NH_4OH$ solution is used to quench the reaction and to remove the Cu(I) catalyst by forming the water soluble copper complex. The aqueous solution is usually extracted with an organic solvent, such as ethyl acetate, several times. Approximately, 90–95% of the desired coupling product can be recovered from the reaction mixture. Activated carbon is employed, if necessary, to decolorize the organic extracts. Pale-yellow to off-white crystals are usually obtained as the crude product in good to excellent yield (65–85%) and quality (>95% pure). The better quality of the material (>99% pure) can be obtained from one simple recrystallization of the crude material from an organic solvent or an organic solvent system, such as ethyl acetate and heptane.

Other features of the invention will become apparent in the course of the following descriptions of exemplary embodiments that are given for illustration of the invention and are not intended to be limiting thereof.

EXAMPLES

Example 1

1-(4-Amino-3-fluoro)phenyl-2-(N,N-dimethylamino)methylimidazole (9, 9)

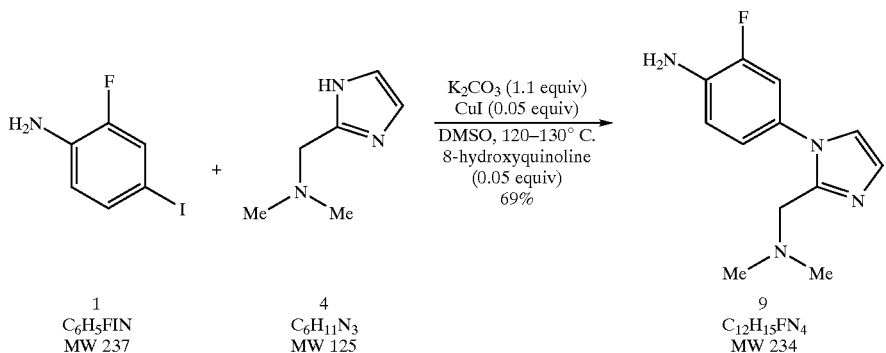

| Substrates/Reagents | MW | W | d | V | mol | mol/mol |
|---|---|---|---|---|---|---|
| 1 | 237 | 71.1 g | | | 0.3 mol | 1 |
| 4 | 125 | 41.25 g | | | 0.33 mol | 1.1 |
| CuI | 190 | 2.85 g | | | 0.015 mol | 0.05 |
| K$_2$CO$_3$ (powder, −325 mesh) | 138 | 43.47 g | | | 0.315 mol | 1.05 |
| 8-hydroxyquinoline | 145 | 2.18 g | | | 0.015 mol | 0.05 |
| DMSO | | | | 300 mL | | |

To a 1.0 L three neck round bottom flask equipped with a magnetic stirrer and a thermocouple was charged 2-fluoro-4-iodoaniline (1, 71.1 g, 0.3 mol), 2-(N,N-dimethylamino) methylimidazole (4, 41.25 g, 0.33 mol, 1.1 equiv), powder K$_2$CO$_3$ (325 mesh, 43.47 g, 0.315 mol, 1.05 equiv), 8-hydroxyquinoline (2.18 g, 0.015 mol, 0.05 equiv), and anhydrous DMSO (300 mL, 1.0 M) at room temperature (22–23° C.) under N$_2$. The mixture was then degassed three times with a vacuum/nitrogen cycle ending on nitrogen before being charged with powder CuI (2.85 g, 0.015 mol, 0.05 equiv). The resulting reaction mixture was degassed three times again with a vacuum/nitrogen cycle ending on nitrogen before being warmed to 120–125° C. When the reaction was deemed complete after 16 h at 120–125° C. (1 A %<5% at 254 nm via HPLC analysis), the dark brown reaction mixture was cooled to 40–50° C. A 14% aqueous NH$_4$OH solution (600 mL, prepared from 28% concentrated ammonium hydroxide solution) was then added to the reaction mixture at 40–50° C., and the resulting mixture was agitated for 1 h at 20–25° C. The mixture was then transferred into a separation funnel, and the flask was washed with water (50 mL) and ethyl acetate (EtOAc, 100 mL). The aqueous solution was then extracted with EtOAc (1×1000 mL and 2×500 mL). The combined ethyl acetate extracts were then washed with saturated NH$_4$Cl aqueous solution (2×200 mL), dried over MgSO$_4$ (30 g), filtered through a Celite bed, and concentrated in vacuo at 45–50° C. The residual slurry of the crude 1-(4-amino-3-fluoro)phenyl-2-(N,N-dimethylamino)methylimidazole (9) in about 200 mL of ethyl acetate was subsequently warmed to reflux (77–78° C.) to give a brown to black solution. Heptane (80 mL) were then added to the solution at 70° C., and the solution was cooled to 45–50° C. before being treated with active carbon (charcoal, 4 g). The mixture was warmed to reflux again for 1 h before being filtered through a Celite bed at 50–55° C. The Celite bed was washed with 20 mL of ethyl acetate, and the combined filtrates and washing solution were poured back into a clean 500 mL round bottom flask. A total of 120 mL of ethyl acetate was then distilled off in vacuo at 45–50° C., and an additional 100 mL of heptane were added into the flask at 50° C. The mixture was then gradually cooled to 20–25° C. and stirred at 20–25° C. for 1 h before being cooled to 5–10° C. for 2 h to precipitate the desired product, 1-(4-amino-3-fluoro)phenyl-2-(N,N-dimethylamino)-methylimidazole (9). The solids were collected by filtration and washed with 20% (v/v) of tert-butyl methyl ether (TBME)/heptane (2×20 mL) before being dried in vacuo with nitrogen purge at 40–45° C. to a constant weight. The first crop of the desired 1-(4-amino-3-fluoro)phenyl-2-(N, N-dimethylamino)methylimidazole (9, 42.3 g, 70.2 g theoretical, 60.3%) was obtained as pale-yellow crystals, which was found to be essentially pure (>99.5 A % and >99.5 wt % by HPLC) and can be used in the following reaction without further purification. The combined mother liquor and washing solution was then concentrated in vacuo to afford the second crop of the desired product (9, 6.2 g, 70.2 g theoretical, 8.8%; a total of 69.1% yield) as pale-yellow crystals. The analytically pure 9 was obtained by recrystallization of the crude 9 from ethyl acetate and heptane. For 9: white crystals; mp 125° C. (ethyl acetate/hexane); CIMS ml/z 234.9 (M$^+$+H, C$_{12}$H$_{15}$FN$_4$).

Example 2

1-(4-Amino-3-fluoro)phenyl-2-(N,N-dimethylamino)methylimidazole (9, 9)

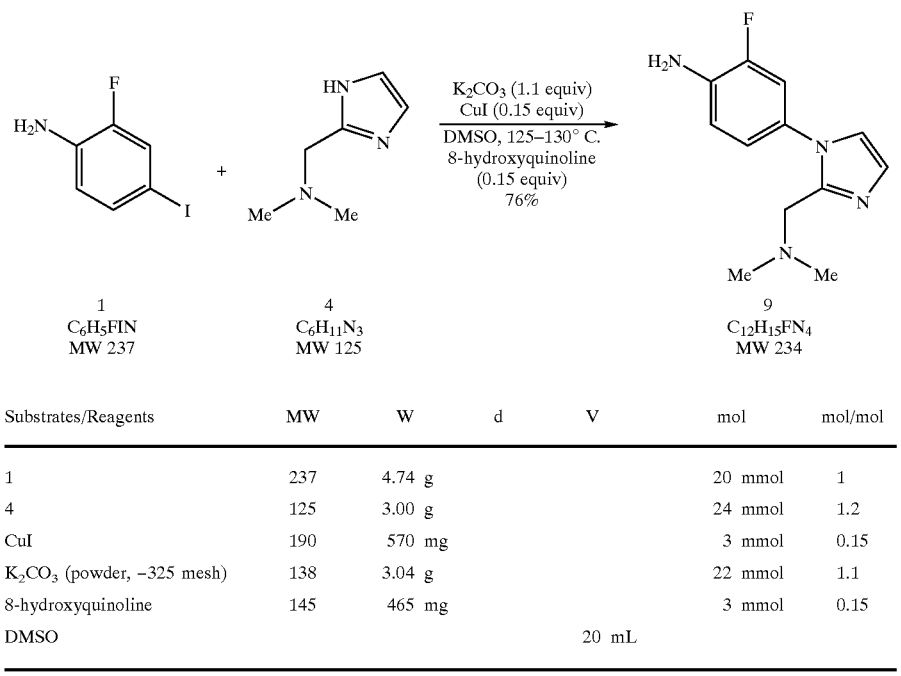

| Substrates/Reagents | MW | W | d | V | mol | mol/mol |
|---|---|---|---|---|---|---|
| 1 | 237 | 4.74 g | | | 20 mmol | 1 |
| 4 | 125 | 3.00 g | | | 24 mmol | 1.2 |
| CuI | 190 | 570 mg | | | 3 mmol | 0.15 |
| K$_2$CO$_3$ (powder, −325 mesh) | 138 | 3.04 g | | | 22 mmol | 1.1 |
| 8-hydroxyquinoline | 145 | 465 mg | | | 3 mmol | 0.15 |
| DMSO | | | | 20 mL | | |

A suspension of 2-fluoro-4-iodoaniline (1, 4.74 g, 20 mmol), 2-(N,N-dimethylamino)methylimidazole (4, 3.0 g, 24 mmol, 1.2 equiv), powder K$_2$CO$_3$ (325 mesh, 3.04 g, 22 mmol, 1.1 equiv), 8-hydroxyquinoline (465 mg, 3.0 mmol, 0.15 equiv) in anhydrous DMSO (20 mL, 1.0 M) at room temperature (22–23° C.) was degassed three times with a vacuum/nitrogen cycle ending on nitrogen before being charged with powder CuI (570 mg, 3.0 mmol, 0.15 equiv). The resulting reaction mixture was degassed three times again with a vacuum/nitrogen cycle ending on nitrogen before being warmed to 120–125° C. When the reaction was deemed complete after 6 h at 120–125° C. (1 A %<5% at 254 nm via HPLC analysis), the dark brown reaction mixture was cooled to 40–50° C. A 14% aqueous NH$_4$OH solution (20 mL, prepared from 28% concentrated ammonium hydroxide solution) was then added to the reaction mixture at 40–50° C., and the resulting mixture was agitated for 1 h at 20–25° C. The mixture was then transferred into a separation funnel, and the flask was washed with water (10 mL) and ethyl acetate (EtOAc, 50 mL). The aqueous solution was then extracted with EtOAc (3×50 mL). The combined ethyl acetate extracts were then washed with saturated NH$_4$Cl aqueous solution (2×20 mL), dried over MgSO$_4$, filtered through a Celite bed, and concentrated in vacuo at 45–50° C. The residual slurry of the crude 9 in about 30 mL of ethyl acetate was subsequently warmed to reflux (77–78° C.) to give a brown to black solution. Heptane (20 mL) were then added to the solution at 70° C., and the solution was cooled to 45–50° C. before being treated with active carbon (charcoal, 0.5 g). The mixture was warmed to reflux again for 1 h before being filtered through a Celite bed at 50–55° C. The Celite bed was washed with 10 mL of ethyl acetate, and the combined filtrates and washing solution were poured back into a clean 100 mL round bottom flask. A total of 25 mL of ethyl acetate was then distilled off in vacuo at 45–50° C., and an additional 20 mL of heptane were added into the flask at 50° C. The mixture was then gradually cooled to 20–25° C. and stirred at 20–25° C. for 1 h before being cooled to 5–10° C. for 2 h to precipitate the desired product (9). The solids were collected by filtration and washed with 20% (v/v) of tert-butyl methyl ether (TBME)/heptane (2×20 mL) before being dried in vacuo with nitrogen purge at 40–45° C. to a constant weight. The desired product (9, 3.56 g, 4.68 g theoretical, 76%) was obtained as pale-yellow crystals, which was found to be identical in every comparable aspect with the sample made from example 1. The crude 9 was found to be essentially pure and can be used in the following reaction without further purification.

Example 3

1-(4-Amino-3-fluoro)phenyl-2-methylimidazole (10)

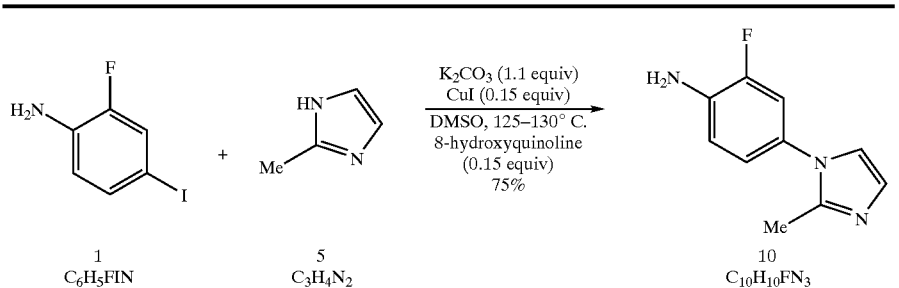

| Substrates/Reagents | MW | W | d | V | mol | mol/mol |
|---|---|---|---|---|---|---|
| 1 | 237 | 4.74 g | | | 20 mmol | 1 |
| 5,2-methylimidazole | 82 | 1.97 g | | | 24 mmol | 1.2 |
| CuI | 190 | 570 mg | | | 3 mmol | 0.15 |
| $K_2CO_3$ (powder, −325 mesh) | 138 | 3.04 g | | | 22 mmol | 1.1 |
| 8-hydroxyquinoline | 145 | 465 mg | | | 3 mmol | 0.15 |
| DMSO | | | | 20 mL | | |

Following the procedure detailed in example 2, 2-fluoro-4-iodoaniline (1, 4.74 g, 20 mmol) and 2-methylimidazole (5, 1.97 g, 24 mmol, 1.2 equiv) were coupled under the ligand-accelerated Cu(I)-catalyzed condition to generate 1-(4-amino-3-fluoro)phenyl-2-methylimidazole (10, 2.87 g, 3.82 g theoretical, 75%) as white crystals. For 10: white crystals; mp 95.6° C. (ethyl acetate/hexane); CIMS m/z 191.9 ($M^+$+H, $C_{10}H_{10}FN_3$).

Example 4

1-(4-Amino-3-fluoro)phenylimidazole (11)

Following the procedure detailed in example 2, 2-fluoro-4-iodoaniline (1, 4.74 g, 20 mmol) and imidazole (6, 1.63 g, 24 mmol, 1.2 equiv) were coupled under the ligand-accelerated Cu(I)-catalyzed condition to generate 1-(4-amino-3-fluoro)phenylimidazole (11, 2.83 g, 3.54 g theoretical, 80%) as white crystals. For 11: white crystals; mp 98.6° C. (ethyl acetate/hexane); CIMS m/z 177.8 ($M^+$+H, $C_9H_8FN_3$).

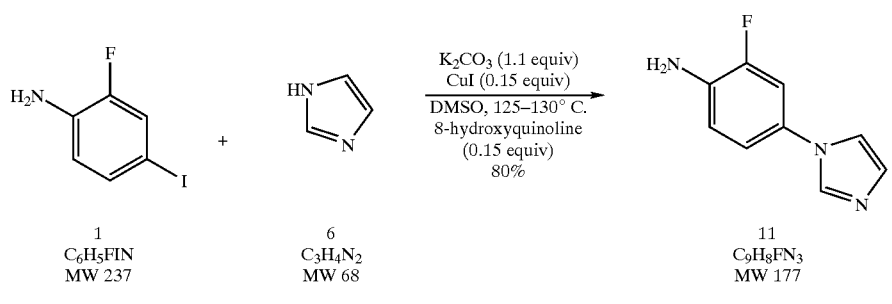

| Substrates/Reagents | MW | W | d | V | mol | mol/mol |
|---|---|---|---|---|---|---|
| 1 | 237 | 4.74 g | | | 20 mmol | 1 |
| 6,imidazole | 68 | 1.63 g | | | 24 mmol | 1.2 |
| CuI | 190 | 570 mg | | | 3 mmol | 0.15 |
| $K_2CO_3$ (powder, −325 mesh) | 138 | 3.04 g | | | 22 mmol | 1.1 |
| 8-hyderoxyquinoline | 145 | 465 mg | | | 3 mmol | 0.15 |
| DMSO | | | | 20 mL | | |

Example 5

1-(4-Amino-3-fluoro)phenyl-2-aminoimidazole (12)

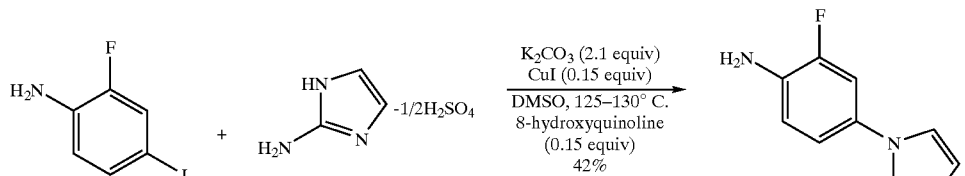

| Substrates/Reagents | MW | W | d | V | mol | mol/mol |
|---|---|---|---|---|---|---|
| 1 | 237 | 4.74 g | | | 20 mmol | 1 |
| 7,2-aminoimidazole sulfate | 132 | 3.17 g | | | 24 mmol | 1.2 |
| CuI | 190 | 570 mg | | | 3 mmol | 0.15 |
| $K_2CO_3$ (powder, −325 mesh) | 138 | 5.80 g | | | 42 mmol | 2.1 |
| 8-hydroxyquinoline | 145 | 465 mg | | | 3 mmol | 0.15 |
| DMSO | | | | 20 mL | | |

Following the procedure detailed in example 2, 2-fluoro-4-iodoaniline (1, 4.74 g, 20 mmol) and 2-aminoimidazole sulfate (7, 3.17 g, 24 mmol, 1.2 equiv) were coupled under the ligand-accelerated Cu(I)-catalyzed condition to generate 1-(4-amino-3-fluoro)phenyl-2-aminoimidazole (12, 1.61 g, 3.84 g theoretical, 42%) as brown oil, which solidified upon standing at room temperature in vacuo. For 12: CIMS m/z 192.9 ($M^+$+H, $C_9H_9FN_4$).

Following the procedure detailed in example 2, 2-fluoro-4-iodoaniline (1, 4.74 g, 20 mmol) and 2-methylimidazole (5, 3.46 g, 24 mmol, 1.2 equiv) were coupled under the ligand-accelerated Cu(I)-catalyzed -condition to generate 1-(4-amino-3-fluoro)phenyl-4-phenylimidazole (13, 4.10 g, 5.06 g theoretical, 81%) as white crystals. For 10: white crystals; mp 130.1° C. (ethyl acetate/hexane); CIMS m/z 253.9 ($M^+$+H, $C_{15}H_{12}FN_3$).

Example 6

1-(4-Amino-3-fluoro)phenyl-4-phenylimidazole (13)

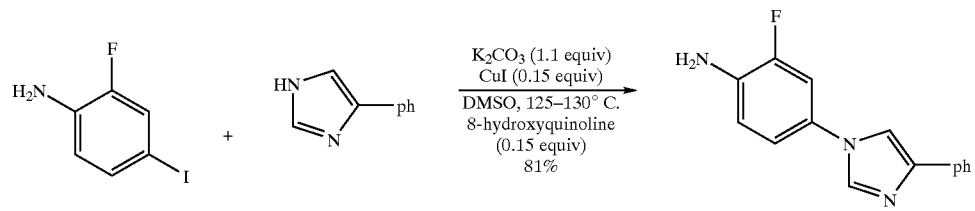

| Substrates/Reagents | MW | W | d | V | mol | mol/mol |
|---|---|---|---|---|---|---|
| 1 | 237 | 4.74 g | | | 20 mmol | 1 |
| 8,4-phenylimidazole | 144 | 3.46 g | | | 24 mmol | 1.2 |
| CuI | 190 | 570 mg | | | 3 mmol | 0.15 |
| $K_2CO_3$ (powder, −325 mesh) | 138 | 3.04 g | | | 22 mmol | 1.1 |
| 8-hydroxyquinoline | 145 | 465 mg | | | 3 mmol | 0.15 |
| DMSO | | | | 20 mL | | |

Example 7

1-(3-Amino)phenyl-2-(N,N-dimethylamino)methylimidazole (14)

| Substrates/Reagents | MW | W | d | V | mol | mol/mol |
|---|---|---|---|---|---|---|
| 2,3-iodoaniline | 219 | 4.38 g | | | 20 mmol | 1 |
| 4 | 125 | 3.00 g | | | 24 mmol | 1.2 |
| CuI | 190 | 570 mg | | | 3 mmol | 0.15 |
| $K_2CO_3$ (powder, −325 mesh) | 138 | 3.04 g | | | 22 mmol | 1.1 |
| 8-hydroxyquinoline | 145 | 465 mg | | | 3 mmol | 0.15 |
| DMSO | | | | 20 mL | | |

Following the procedure detailed in example 2, 3-iodoaniline (2, xx g, 20 mmol) and 2-(N,N-dimethylamino)methylimidazole (4, 3.0 g, 24 mmol, 1.2 equiv) were coupled under the ligand-accelerated Cu(I)-catalyzed condition to generate 1-(3-amino)phenyl-2-(N,N-dimethylamino)methylimidazole (14, 2.46 g, 4.32 g theoretical, 57%) as pale-yellow oil, which solidified at room temperature in vacuo. For 14: CIMS m/z 216.9 ($M^+$+H, $C_{12}H_{16}N_4$)

Example 8

1-(3-Amino)phenyl-2-methylimidazole (15)

Following the procedure detailed in example 2, 3-iodoaniline (2, 4.38 g, 20 mmol) and 2-methylimidazole (5, 1.97 g, 24 mmol, 1.2 equiv) were coupled under the ligand-accelerated Cu(I)-catalyzed condition to generate 1-(3-amino)phenyl-2-methylimidazole (15, 2.49 g, 3.46 g theoretical, 72%) as white crystals. For 15: white crystals; mp 122.5° C. (ethyl acetate/hexane); CIMS m/z 173.9 ($M^+$+H, $C_{10}H_{11}N_3$)

| Substrates/Reagents | MW | W | d | V | mol | mol/mol |
|---|---|---|---|---|---|---|
| 2,3-iodoaniline | 219 | 4.38 g | | | 20 mmol | 1 |
| 5,2-methylimidazole | 82 | 1.97 g | | | 24 mmol | 1.2 |
| CuI | 190 | 570 mg | | | 3 mmol | 0.15 |
| $K_2CO_3$ (powder, −325 mesh) | 138 | 3.04 g | | | 22 mmol | 1.1 |
| 8-hydroxyquinoline | 145 | 465 mg | | | 3 mmol | 0.15 |
| DMSO | | | | 20 mL | | |

Example 9

1-(3-Amino)phenylimidazole (16)

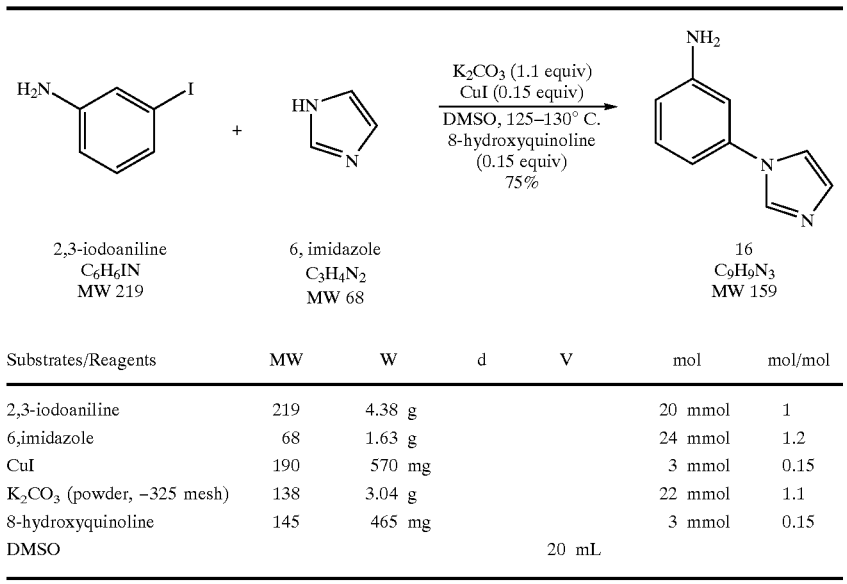

| Substrates/Reagents | MW | W | d | V | mol | mol/mol |
|---|---|---|---|---|---|---|
| 2,3-iodoaniline | 219 | 4.38 g | | | 20 mmol | 1 |
| 6,imidazole | 68 | 1.63 g | | | 24 mmol | 1.2 |
| CuI | 190 | 570 mg | | | 3 mmol | 0.15 |
| $K_2CO_3$ (powder, −325 mesh) | 138 | 3.04 g | | | 22 mmol | 1.1 |
| 8-hydroxyquinoline | 145 | 465 mg | | | 3 mmol | 0.15 |
| DMSO | | | | 20 mL | | |

Following the procedure detailed in example 2, 3-iodoaniline (2, 4.38 g, 20 mmol) and imidazole (6, 1.63 g, 24 mmol, 1.2 equiv) were coupled under the ligand-accelerated Cu(I)-catalyzed condition to generate 1-(3-amino)phenylimidazole (16, 2.38 g, 3.18 g theoretical, 75%) as white crystals. For 16: white crystals; mp 113.4° C. (ethyl acetate/hexane); CIMS m/z 159.9 ($M^+$+H, $C_9H_9N_3$).

Example 10

1-(3-Amino)phenyl-2-aminoimidazole (17)

Following the procedure detailed in example 2, 3-iodoaniline (2, 4.38 g, 20 mmol) and 2-aminoimidazole sulfate (7, 3.17 g, 24 mmol, 1.2 equiv) were coupled under the ligand-accelerated Cu(I)-catalyzed condition to generate 1-(3-amino)phenyl-2-aminoimidazole (17, 1.39 g, 3.48 g theoretical, 40%) as yellow to brown oil, which solidified upon standing at room temperature in vacuo. For 17: CIMS m/z 174.8 ($M^+$+H, $C_9H_9N_4$).

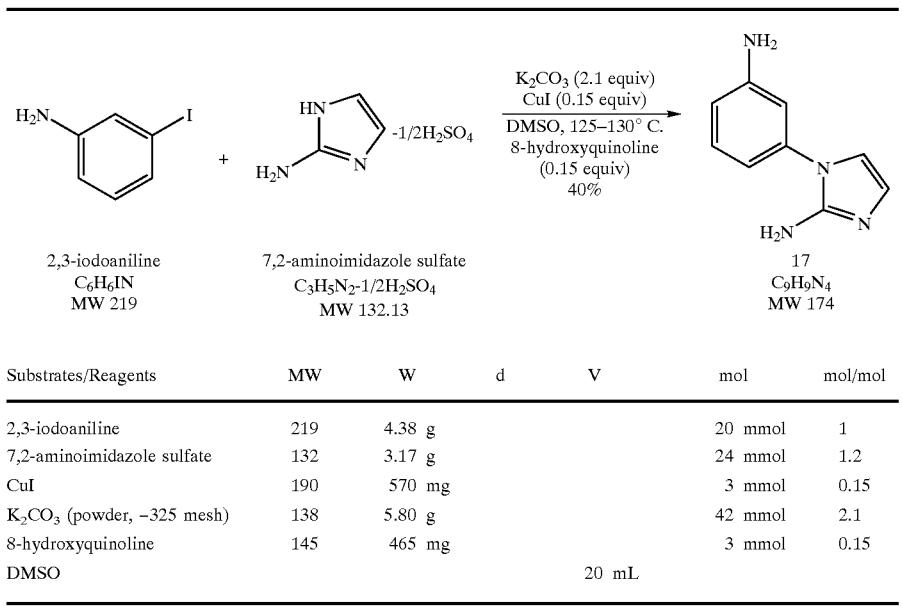

| Substrates/Reagents | MW | W | d | V | mol | mol/mol |
|---|---|---|---|---|---|---|
| 2,3-iodoaniline | 219 | 4.38 g | | | 20 mmol | 1 |
| 7,2-aminoimidazole sulfate | 132 | 3.17 g | | | 24 mmol | 1.2 |
| CuI | 190 | 570 mg | | | 3 mmol | 0.15 |
| $K_2CO_3$ (powder, −325 mesh) | 138 | 5.80 g | | | 42 mmol | 2.1 |
| 8-hydroxyquinoline | 145 | 465 mg | | | 3 mmol | 0.15 |
| DMSO | | | | 20 mL | | |

Example 11

1-(3-Amino)phenyl-4-phenylimidazole (18)

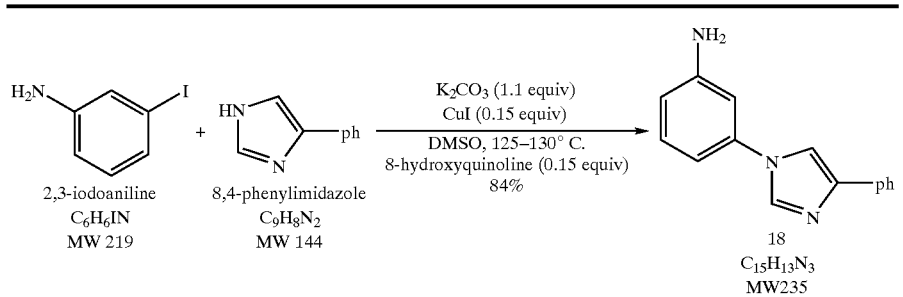

| Substrates/Reagents | MW | W | d | V | mol | mol/mol |
|---|---|---|---|---|---|---|
| 2,3-iodoaniline | 219 | 4.38 g | | | 20 mmol | 1 |
| 8,4-phenylimidazole | 144 | 3.46 g | | | 24 mmol | 1.2 |
| CuI | 190 | 570 mg | | | 3 mmol | 0.15 |
| $K_2CO_3$ (powder, −325 mesh) | 138 | 3.04 g | | | 22 mmol | 1.1 |
| 8-hydroxyquinoline | 145 | 465 mg | | | 3 mmol | 0.15 |
| DMSO | | | | 20 mL | | |

Following the procedure detailed in example 2, 3-iodoaniline (2, 4.38 g, 20 mmol) and 4-phenylimidazole (8, 3.46 g, 24 mmol, 1.2 equiv) were coupled under the ligand-accelerated Cu(I)-catalyzed condition to generate 1-(3-amino)phenyl-4-phenylimidazole (18, 3.95 g, 4.7 g theoretical, 84%) as white crystals. For 18: white crystals; mp 103.7° C. (ethyl acetate/hexane); CIMS m/z 235.9 ($M^+$+H, $C_{15}H_{13}N_3$).

Example 12

1-(2-Amino)phenyl-2-(N,N-dimethylamino)methylimidazole (19)

Following the procedure detailed in example 2, 2-iodoaniline (3, 4.38 g, 20 mmol) and 2-(N,N-dimethylamino)methylimidazole (4, 3.0 g, 24 mmol, 1.2 equiv) were coupled under the ligand-accelerated Cu(I)-catalyzed condition to generate 1-(2-amino)phenyl-2-(N,N-dimethylamino)methylimidazole (19, 2.72 g, 4.32 g theoretical, 63%) as white crystals. For 19: white crystals; mp 120.1° C. (ethyl acetate/hexane); CIMS m/z 216.9 ($M^+$+H, $C_{12}H_{16}N_4$).

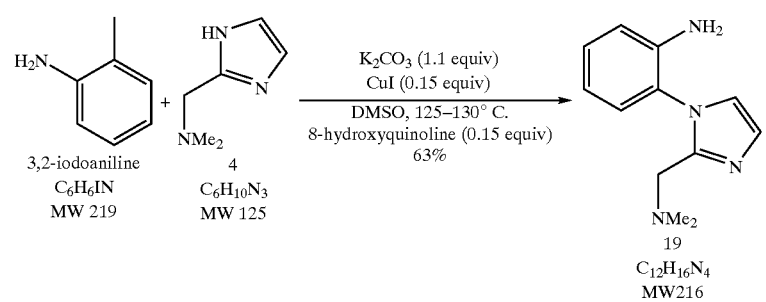

| Substrates/Reagents | MW | W | d | V | mol | mol/mol |
|---|---|---|---|---|---|---|
| 3,2-iodoaniline | 219 | 4.38 g | | | 20 mmol | 1 |
| 4 | 125 | 3.00 g | | | 24 mmol | 1.2 |
| CuI | 190 | 570 mg | | | 3 mmol | 0.15 |
| $K_2CO_3$ (powder, −325 mesh) | 138 | 3.04 g | | | 22 mmol | 1.1 |
| 8-hydroxyquinoline | 145 | 465 mg | | | 3 mmol | 0.15 |
| DMSO | | | | 20 mL | | |

Example 13

1-(2-Amino)phenyl-2-methylimidazole (20)

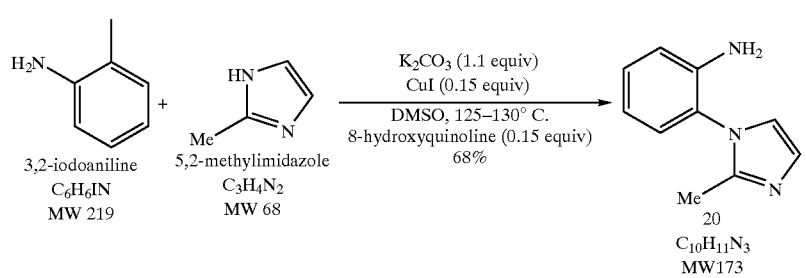

| Substrates/Reagents | MW | W | d | V | mol | mol/mol |
|---|---|---|---|---|---|---|
| 3,2-iodoaniline | 219 | 4.38 g | | | 20 mmol | 1 |
| 5,2-methylimidazole | 82 | 1.97 g | | | 24 mmol | 1.2 |
| CuI | 190 | 570 mg | | | 3 mmol | 0.15 |
| $K_2CO_3$ (powder, −325 mesh) | 138 | 3.04 g | | | 22 mmol | 1.1 |
| 8-hydroxyquinoline | 145 | 465 mg | | | 3 mmol | 0.15 |
| DMSO | | | | 20 mL | | |

Following the procedure detailed in example 2, 2-iodoaniline (3, 4.38 g, 20 mmol) and 2-methylimidazole (5, 1.97 g, 24 mmol, 1.2 equiv) were coupled under the ligand-accelerated Cu(I)-catalyzed condition to generate 1-(2-amino)phenyl-2-methylimidazole (20, 2.35 g, 3.46 g theoretical, 68%) as white crystals. For 20: white crystals; mp 136.7° C. (ethyl acetate/hexane); CIMS m/z 173.8 ($M^++H$, $C_{10}H_{11}N_3$).

Example 14

1-(2-Amino)phenylimidazole (21)

Following the procedure detailed in example 2, 2-iodoaniline (3, 4.38 g, 20 mmol) and imidazole (6, 1.63 g, 24 mmol, 1.2 equiv) were coupled under the ligand-accelerated Cu(I)-catalyzed condition to generate 1-(2-amino)phenylimidazole (21, 2.32 g, 3.18 g theoretical, 73%) as white crystals. For 21: white crystals; mp 108° C. (ethyl acetate/hexane); CIMS m/z 159.9 ($M^++H$, $C_9H_9N_3$).

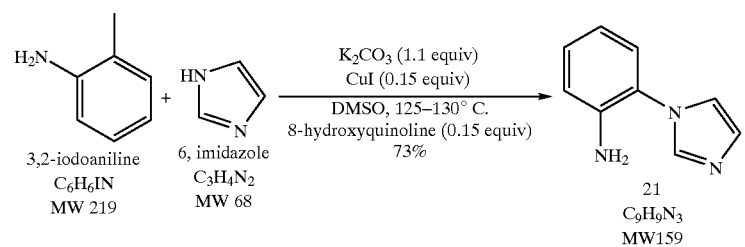

| Substrates/Reagents | MW | W | d | V | mol | mol/mol |
|---|---|---|---|---|---|---|
| 3,2-iodoaniline | 219 | 4.38 g | | | 20 mmol | 1 |
| 6, imidazole | 68 | 1.63 g | | | 24 mmol | 1.2 |
| CuI | 190 | 570 mg | | | 3 mmol | 0.15 |
| $K_2CO_3$ (powder, −325 mesh) | 138 | 3.04 g | | | 22 mmol | 1.1 |
| 8-hydroxyquinoline | 145 | 465 mg | | | 3 mmol | 0.15 |
| DMSO | | | | 20 mL | | |

Example 15

1-(2-Amino)phenyl-2-aminoimidazole (22)

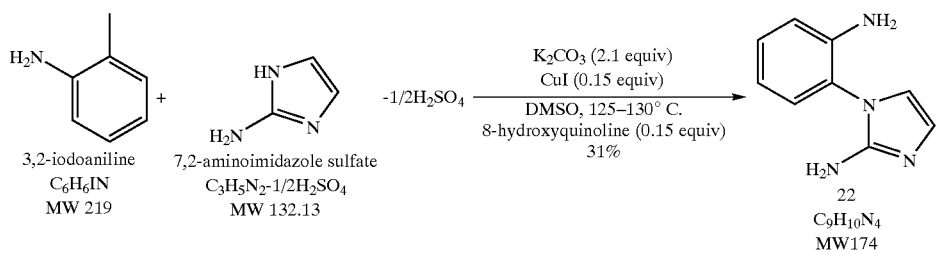

| Substrates/Reagents | MW | W | d | V | mol | mol/mol |
|---|---|---|---|---|---|---|
| 3,2-iodoaniline | 219 | 4.38 g | | | 20 mmol | 1 |
| 7,2-aminoimidazale sulfate | 132 | 3.17 g | | | 24 mmol | 1.2 |
| CuI | 190 | 570 mg | | | 3 mmol | 0.15 |
| $K_2CO_3$ (powder, −325 mesh) | 138 | 5.80 g | | | 42 mmol | 2.1 |
| 8-hydroxyquinoline | 145 | 465 mg | | | 3 mmol | 0.15 |
| DMSO | | | | 20 mL | | |

Following the procedure detailed in example 2, 2-iodoaniline (3, 4.38 g, 20 mmol) and 2-aminoimidazole sulfate (7, 3.17 g, 24 mmol, 1.2 equiv) were coupled under the ligand-accelerated Cu(I)-catalyzed condition to generate 1-(2-amino)phenyl-2-aminoimidazole (22, 1.08 g, 3.48 g theoretical, 31%) as pale-yellow oil, which solidified upon standing at room temperature in vacuo. For 22: CIMS m/z 174.8 ($M^+$+H, $C_9H_{10}N_4$).

Example 16

1-(2-Amino)phenyl-4-phenylimidazole (23)

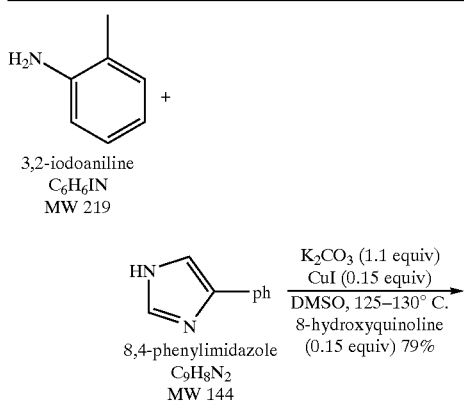

-continued

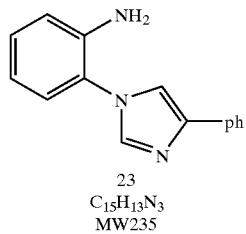

| Substrates/Reagents | MW | W | d | V | mol | mol/mol |
|---|---|---|---|---|---|---|
| 3,2-iodoaniline | 219 | 4.38 g | | | 20 mmol | 1 |
| 8,4-phenylimidazole | 144 | 3.46 g | | | 24 mmol | 1.2 |
| CuI | 190 | 570 mg | | | 3 mmol | 0.15 |
| $K_2CO_3$ (powder, −325 mesh) | 138 | 3.04 g | | | 22 mmol | 1.1 |
| 8-hydroxy-quinoline | 145 | 465 mg | | | 3 mmol | 0.15 |
| DMSO | | | | 20 mL | | |

Following the procedure detailed in example 2, 2-iodoaniline (3, 4.38 g, 20 mmol) and 4-phenylimidazole (8, 3.46 g, 24 mmol, 1.2 equiv) were coupled under the ligand-accelerated Cu(I)-catalyzed condition to generate 1-(2-amino)phenyl-4-phenylimidazole (23, 3.7 g, 4.7 g theoretical, 79%) as white crystals. For 23: white crystals; mp 121.4° C. (ethyl acetate/hexane); CIMS m/z 235.9 ($M^+$+H, $C_{15}H_{13}N_3$).

Example 17

1-(4-Amino-3-fluoro)phenyl-2-(N,N-dimethylamino)methylimidazole (9, 9)

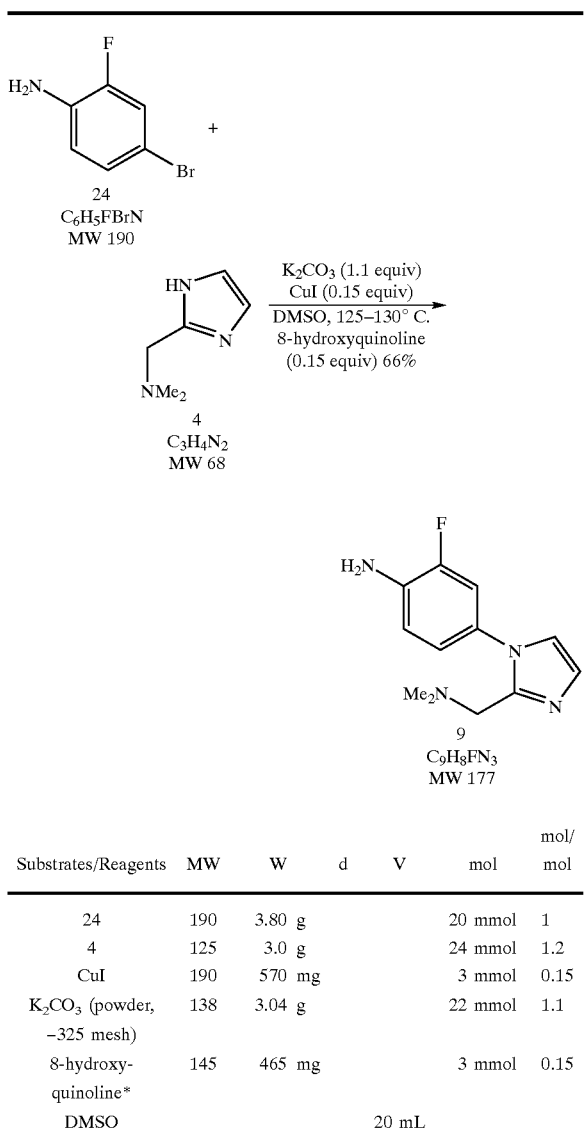

| Substrates/Reagents | MW | W | d | V | mol | mol/mol |
|---|---|---|---|---|---|---|
| 24 | 190 | 3.80 g | | | 20 mmol | 1 |
| 4 | 125 | 3.0 g | | | 24 mmol | 1.2 |
| CuI | 190 | 570 mg | | | 3 mmol | 0.15 |
| K₂CO₃ (powder, −325 mesh) | 138 | 3.04 g | | | 22 mmol | 1.1 |
| 8-hydroxy-quinoline* | 145 | 465 mg | | | 3 mmol | 0.15 |
| DMSO | | | | 20 mL | | |

Following the procedure detailed in example 2, 2-fluoro-4-bromoaniline (24, 3.80 g, 20 mmol) and 2-(N,N-dimethylamino)methylimidazole (4, 3.0 g, 24 mmol, 1.2 equiv) were coupled under the ligand-accelerated Cu(I)-catalyzed condition at 125–130° C. for 12 h to generate 1-(4-amino-3-fluoro)phenyl-2-(N,N-dimethylamino)methylimidazole (9, 3.09 g, 4.68 g theoretical, 66%) as white crystals, which was identical with the material prepared from example 1 and example 2 in every comparable aspect.

Example 18

1-(4-Amino-3-fluoro)phenylimidazole (11)

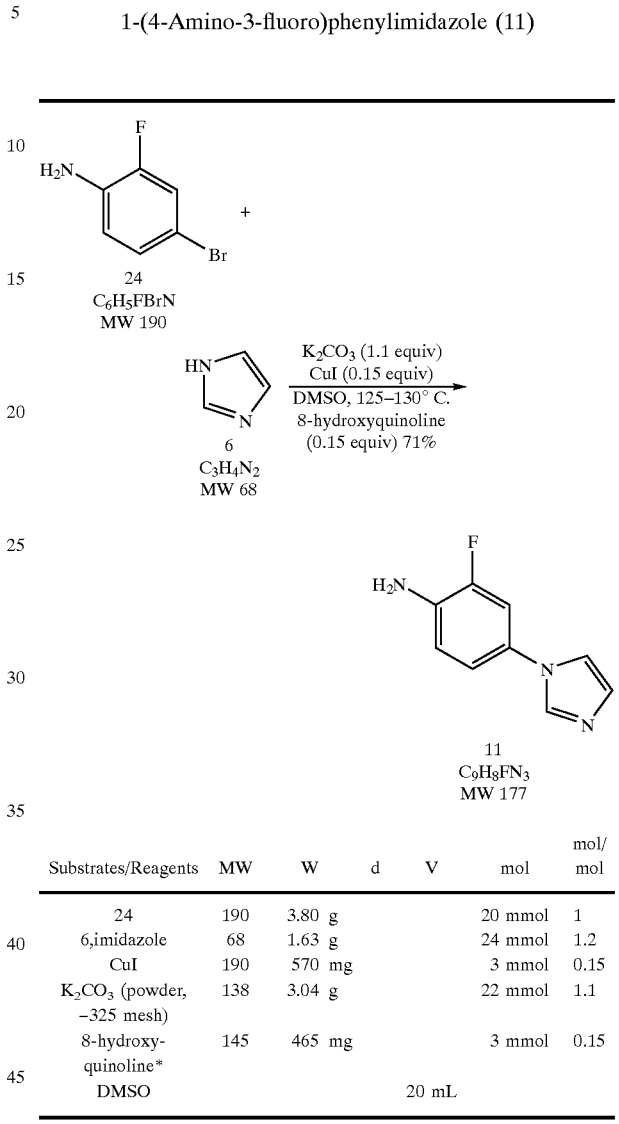

| Substrates/Reagents | MW | W | d | V | mol | mol/mol |
|---|---|---|---|---|---|---|
| 24 | 190 | 3.80 g | | | 20 mmol | 1 |
| 6, imidazole | 68 | 1.63 g | | | 24 mmol | 1.2 |
| CuI | 190 | 570 mg | | | 3 mmol | 0.15 |
| K₂CO₃ (powder, −325 mesh) | 138 | 3.04 g | | | 22 mmol | 1.1 |
| 8-hydroxy-quinoline* | 145 | 465 mg | | | 3 mmol | 0.15 |
| DMSO | | | | 20 mL | | |

Following the procedure detailed in example 2, 2-fluoro-4-bromoaniline (24, 3.80 g, 20 mmol) and imidazole (6, 1.63 g, 24 mmol, 1.2 equiv) were coupled under the ligand-accelerated Cu(I)-catalyzed condition at 125–130° C. for 8 h to generate 1-(4-amino-3-fluoro)phenylimidazole (11, 2.51 g, 3.54 g theoretical, 71%) as white crystals, which was identical with the material prepared from example 4 in every comparable aspect.

Numerous modifications and variations of the present invention are possible in light of the above teachings. It is therefore to be understood that within the scope of the appended claims, the invention may be practiced otherwise than as specifically described herein.

What is claimed is:

1. A process for making a compound of Formula III

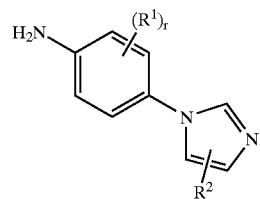

III wherein:
in Formula III, from 0–1 of the carbon atoms of the 6-membered ring are replaced with N;
comprising: reacting an aniline of Formula IV with an azole of Formula V in the presence of $Cu(I)X^1$ and a bidentate ligand:

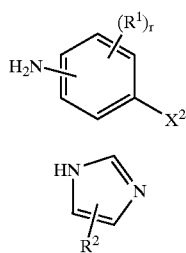

IV

V wherein:
in Formula IV, from 0–1 of the carbon atoms are replaced with N;
$X^1$ is selected from Cl, Br, I, and SCN;
$X^2$ is selected from Br or I;
$R^1$ is selected from H, Cl, F, Br, I, $C_{1-4}$ alkyl, $C_{1-4}$ alkoxy, $C_{1-4}$ alkylene-O—$C_{1-4}$ alkyl, $NH_2$, $NH(C_{1-4}$ alkyl), $N(C_{1-4}$ alkyl$)_2$, $C_{1-4}$ alkylene-$NH_2$, $C_{1-4}$ alkylene-$NH(C_{1-4}$ alkyl), $C_{1-4}$ alkylene-$N(C_{1-4}$ alkyl$)_2$, $C_{3-10}$ carbocycle substituted with 0–2 $R^3$, and 5–6 membered heterocycle comprising carbon atoms and 1–4 heteroatoms selected from N, O, and S and substituted with 0–2 $R^3$;
$R^2$ is selected from H, Cl, F, Br, I, $C_{1-4}$ alkyl, $C_{1-4}$ alkoxy, $C_{1-4}$ alkylene-O—$C_{1-4}$ alkyl, $NH_2$, $NH(C_{1-4}$ alkyl), $N(C_{1-4}$ alkyl$)_2$, $C_{1-4}$ alkylene-$NH_2$, $C_{1-4}$ alkylene-$NH(C_{1-4}$ alkyl), $C_{1-4}$ alkylene-$N(C_{1-4}$ alkyl$)_2$, $C_{3-10}$ carbocycle substituted with 0–2 $R^3$, and 5–6 membered heterocycle comprising carbon atoms and 1–4 heteroatoms selected from N, O, and S and substituted with 0–2 $R^3$;
$R^3$ is selected from Cl, F, Br, I, $C_{1-4}$ alkyl, $C_{1-4}$ alkoxy, $C_{1-4}$ alkylene-O—$C_{1-4}$ alkyl, $NH_2$, $NH(C_{1-4}$ alkyl), $N(C_{1-4}$ alkyl$)_2$, $C_{1-4}$ alkylene-$NH_2$, $C_{1-4}$ alkylene-$NH(C_{1-4}$ alkyl), $C_{1-4}$ alkylene-$N(C_{1-4}$ alkyl$)_2$, and $NO_2$;
r is 1 or 2; and,
the bidentate ligand is a hydrolytically stabile ligand that is known to ligate with Cu(I) and comprises two heteroatoms selected from N and O.

2. A process according to claim 1, wherein the bidentate ligand is selected from tetramethylethylenediamine (TMED), 2,2'-dipyridyl (DPD), 8-hydroxyquinoline (HQL), and 1,10-phenanthroline (PNT) and from 0.01–0.20 equivalents are present, based on the molar amount of aniline present.

3. A process according to claim 2, wherein the bidentate ligand is 8-hydroxyquinoline (HQL) or 1,10-phenanthroline (PNT) and from 0.05–0.15 equivalents are present.

4. A process according to claim 3, wherein the bidentate ligand is 8-hydroxyquinoline (HQL) and from 0.05–0.15 equivalents are present.

5. A process according to claim 3, wherein the bidentate ligand is 1,10-phenanthroline (PNT) and from 0.05–0.15 equivalents are present.

6. A process according to claim 1, wherein from 0.01–0.20 equivalents of $Cu(I)X^1$ are present, based on the molar amount of aniline present.

7. A process according to claim 6, wherein from 0.05–0.15 equivalents of $Cu(I)X^1$ are present.

8. A process according to claim 7, wherein 0.05 equivalents of $Cu(I)X^1$ are present.

9. A process according to claim 7, 0.15 equivalents of $Cu(I)X^1$ are present.

10. A process according to claim 1, wherein the reacting is performed in the presence of from 1.0–2.0 molar equivalents of base, based on the molar amount of aniline present.

11. A process according to claim 10, wherein the reacting is performed in the presence of from 1.0–1.2 equivalents of $K_2CO_3$.

12. A process according to claim 11, wherein the reacting is performed in the presence of 1.05 equivalents of $K_2CO_3$.

13. A process according to claim 1, wherein from 1–1.5 molar equivalents of azole are used, based on the molar amount of aniline present.

14. A process according to claim 13, wherein from 1.1–1.3, molar equivalents of azole are used, based on the molar amount of aniline present.

15. A process according to claim 14, wherein about 1.2 molar equivalents of azole are used, based on the molar amount of aniline present.

16. A process according to claim 1, wherein the reacting is performed in a polar solvent.

17. A process according to claim 16, wherein the reacting is performed in a polar, aprotic solvent.

18. A process according to claim 17, wherein the reacting is performed in DMSO.

19. A process according to claim 1, wherein the reacting is performed at a temperature of from 100° C. to reflux of the solvent and the reaction is run from 4 to 24 hours.

20. A process according to claim 19, wherein the reacting is performed at a temperature of from 110 to 140° C. and from 6 to 15 hours.

21. A process according to claim 20, wherein the reacting is performed at a temperature of from 120 to 130° C.

22. A process according to claim 1, wherein $X^1$ is I or SCN.

23. A process according to claim 22, wherein $X^1$ is I.

24. A process according to claim 22, wherein $X^1$ is SCN.

25. A process according to claim 1, wherein:
$R^1$ is selected from H, Cl, F, methyl, ethyl, i-propyl, methoxy, and methoxymethylene;
$R^2$ is selected from H, methyl, i-propyl, $NH_2$, $CH_2NH_2$, $CH_2N(CH_3)_2$, and phenyl; and, r is 1.

26. A process according to claim 1, wherein the compound of Formula IV is selected from:

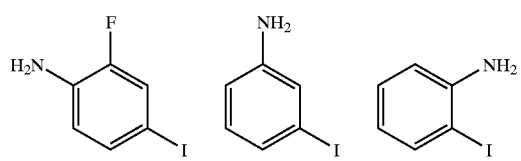
and, the compound of Formula V is selected from:
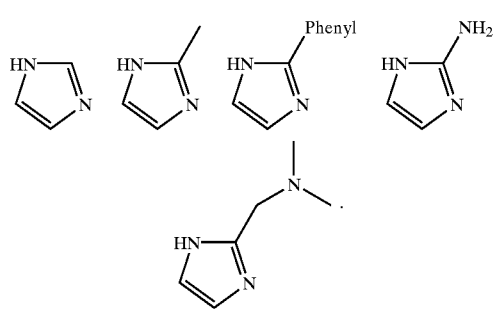
27. A process according to claim 26, wherein the compound of Formula IV is:
and, the compound of Formula V is selected from:
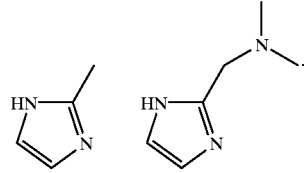
28. A process according to claim 1, wherein the compound of Formula V is:
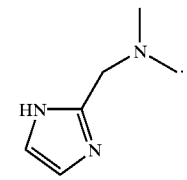
29. A process according to claims 1, wherein the compound of Formula V is:
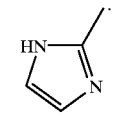
* * * * *